United States Patent
Maekawa et al.

(10) Patent No.: US 9,617,565 B2
(45) Date of Patent: *Apr. 11, 2017

(54) ALCOHOLIC FERMENTATION YEAST AND METHOD FOR PRODUCING ETHANOL USING SAME

(71) Applicants: NIPPON STEEL & SUMIKIN ENGINEERING CO., LTD., Tokyo (JP); EHIME PREFECTURE, Ehime (JP)

(72) Inventors: Natsuki Maekawa, Fukuoka (JP); Yasuhiko Katoh, Fukuoka (JP); Takafumi Kiuchi, Fukuoka (JP); Praneetrattananon Suthasinee, Fukuoka (JP); Shinji Okamoto, Ehime (JP); Kazuko Hirayama, Ehime (JP); Syunsuke Miyaoka, Ehime (JP); Hideaki Tadanobu, Ehime (JP); Masahiko Sudo, Ehime (JP)

(73) Assignees: NIPPON STEEL & SUMIKIN ENGINEERING CO., LTD., Tokyo (JP); EHIME PREFECTURE, Ehime (JP)

( * ) Notice: Subject to any disclaimer, the term of this patent is extended or adjusted under 35 U.S.C. 154(b) by 103 days.

This patent is subject to a terminal disclaimer.

(21) Appl. No.: 14/539,382

(22) Filed: Nov. 12, 2014

(65) Prior Publication Data
US 2015/0132817 A1    May 14, 2015

Related U.S. Application Data

(62) Division of application No. 13/808,965, filed as application No. PCT/JP2011/004415 on Aug. 4, 2011, now Pat. No. 9,187,768.

(30) Foreign Application Priority Data

Aug. 4, 2010  (JP) .................................. 2010-175712

(51) Int. Cl.
| | | |
|---|---|---|
| C12P 7/16 | (2006.01) |
| C12P 7/06 | (2006.01) |
| C12N 1/18 | (2006.01) |
| C12R 1/865 | (2006.01) |
| C12P 7/12 | (2006.01) |

(52) U.S. Cl.
CPC .................. *C12P 7/06* (2013.01); *C12N 1/18* (2013.01); *C12P 7/12* (2013.01); *C12R 1/865* (2013.01); *Y02E 50/17* (2013.01)

(58) Field of Classification Search
None
See application file for complete search history.

(56) References Cited

U.S. PATENT DOCUMENTS

| 4,310,629 A | * | 1/1982 | Muller ..................... C12P 7/06 435/162 |
| 7,540,888 B2 | | 6/2009 | Ryder et al. |
| 2011/0171707 A1 | | 7/2011 | Holt et al. |

FOREIGN PATENT DOCUMENTS

| JP | 2-57176 | 2/1990 |
| JP | 2000-189120 | 7/2000 |
| JP | 2002-153231 | 5/2002 |
| JP | 2002-345464 | 12/2002 |
| JP | 2004-344084 | 12/2004 |
| JP | 2006-75115 | 3/2006 |

OTHER PUBLICATIONS

JP 2002-153231, Machine Translation (Nakazawa et al.), May 28, 2002.*
International Search Report issued Oct. 11, 2011 in International (PCT) Application No. PCT/JP2011/004415.
M. Wilkins et al., "Ethanol production by *Saccharomyces cerevisiae* and *Kluyveromyces marxianus* in the presence of orange-peel oil", World J. Microbiol. Biotechnol., vol. 23, No. 8, pp. 1161-1168, 2007.
J. Bicas et al., "Isolation and screening of D-limonene-resistant microorganisms", Brazilian Journal of Microbiology, vol. 38, pp. 563-567, 2007.
International Preliminary Report on Patentability and Written Opinion issued Mar. 12, 2013 in corresponding International Application No. PCT/JP2011/004415.
Wilkins et al., Process Biochemistry 42 (2007) pp. 1614-1619.

* cited by examiner

*Primary Examiner* — Irene Marx
(74) *Attorney, Agent, or Firm* — Wenderoth, Lind & Ponack, L.L.P.

(57) ABSTRACT

[Problem] To provide an alcoholic fermentation yeast having resistance to limonene, which is a fermentation inhibitor, and a method for producing ethanol using the alcoholic fermentation yeast. [Solution] An alcoholic fermentation yeast *Saccharomyces cerevisiae* (Deposition No. NITE BP-890), which has resistance to limonene and can grow in the presence of limonene at a concentration of 0.1-0.5 wt %, and a method for producing ethanol using the alcoholic fermentation yeast.

6 Claims, 11 Drawing Sheets

FIG. 1

TCTTTGTCCGTGTTTCAAGAGACGGGGCGGCATAAAACCATTAAGCCAGCATCCTTCACTT
ACGTCGCAGTCCTCAGTCCCAGCTGCAGTTCCCACAGCCTAAAATACTTACCGA
GGCAAGCTACATTCGTAGGATTTATCCTGCCACCAAAACTGATGTCTGGCCAGTGA
AATGCGAGATTCCCTACCCAAGGAGCAGGGCACAAAACCATGTCTGATCA
AATGCCCTTCCCTTTCAACAATTTCACGTACTTTTTCACTCTCTCTTTCAAGTTCTTTT
CATCTTTCCATCACTGTACTTGTTCGTATCGGTCTA

ALCOHOLIC FERMENTATION YEAST AND METHOD FOR PRODUCING ETHANOL USING SAME

TECHNICAL FIELD

The present invention relates to an alcoholic fermentation yeast having resistance to limonene, which is a fermentation inhibitor, and to a method for producing ethanol using the alcoholic fermentation yeast.

BACKGROUND ART

Bioethanol, which is an alternative liquid fuel, can be produced by ethanol fermentation of a fruit juice residue extract by yeast added thereto. Such a technique for converting a juice residue extract, or waste, to bioethanol by fermentation is very useful because biomass not competing with food is used as a starting material. In one known ethanol production technique using such a juice residue extract, the juice residue extract is produced from a citrus fruit and concentrated by, for example, centrifugation to obtain a citrus syrup. Then pulp is removed from the citrus syrup, and the resultant citrus syrup is subjected to ethanol fermentation by *Saccharomyces* yeast or the like (see, for example, Patent Literature 1).

CITATION LIST

Patent Literature

Patent Literature 1: Japanese Patent Application Laid-Open No. 2002-153231

SUMMARY OF INVENTION

Technical Problem

Citrus fruits, however, contain limonene (chemical formula: $C_{10}H_{16}$), which is a terpenoid-based oil component, in an amount of 0.2 to 0.5 wt %. It is known that limonene inhibits ethanol fermentation.

Methods for producing ethanol from a citrus-based starting material (juice residue extract) include a first method in which a citrus syrup obtained by concentrating the juice residue extract is used as the starting material and a second method in which the juice residue extract itself is used as the starting material without producing a citrus syrup.

The first method has already been contemplated (see, for example, Japanese Patent Application Laid-Open No. 2002-153231). This method has an advantage in that limonene can be removed in the concentrating step. However, an enormous amount of energy is required in the concentrating step, and the process of fermentation cannot deal with a high-concentration sugar solution, so that the sugar solution must be diluted with water to a sugar concentration of 20% or lower. Therefore, the first method has a problem from the viewpoint of establishing an economical ethanol production method.

In the second method, the juice residue extract contains sugar in an amount of about 10%, and this is an optimal concentration for fermentation. Therefore, if the juice residue extract can be fermented without dilution or concentration, an economical ethanol production process can be established. However, a technique for dealing with limonene which is a fermentation inhibitor must be established.

The most part of limonene is contained in the peel. However, in a juice extraction step and an extract extraction step, the fruit including the peel is mechanically squeezed, and part of limonene is thereby extracted into the juice or extract. The limonene separated from the peel in the above steps is mainly in a micelle form in the juice residue extract. According to the results of measurement performed by the inventors, in the total concentration of limonene contained in a juice residue extract that is total amount of limonene contained in the peel and limonene in a micelle form (being 0.2 to 0.5 wt %), the concentration of limonene in the micelle form was very small, being 0.01 to 0.04 wt %.

However, the results of ethanol fermentation experiments performed using a general yeast with limonene in a micelle (oil) form added to a YPD culture medium showed that the rate of ethanol production decreased rapidly as the concentration of limonene added increased. For example, when 0.1% v/v of limonene was added, the rate of ethanol production was greatly reduced to about 20%. Generally, yeast is present in a sugar solution as fine solid particles and easily adsorbs oily substances. Therefore, the reason for the above-described experimental results may be that the limonene (in an oil form) added in a small amount (0.05% v/v) adsorbed to the yeast, causing fermentation inhibition. To remove limonene, which is a fermentation inhibitor, from a juice residue extract, limonene in a solid form, which accounts for 75% or larger of the total amount of limonene, must be removed, and limonene in a micelle form present as a light liquid (an oily substance) must also be removed. Even when limonene was removed in advance from a starting material by, for example, three-phase centrifugation treatment, fermentation was not stabilized because the conventional general yeast exhibited an induction period, and the fermentation rate was also low. Therefore, fermentability tended to be unstable due to the influence of contamination etc., and it was difficult to maintain high fermentability over a long period of time.

The present invention has been made in view of the foregoing circumstances, and it is an object to provide an alcoholic fermentation yeast having resistance to limonene, which is a fermentation inhibitor, and to provide a method for producing ethanol using the alcoholic fermentation yeast.

Solution to Problem

An alcoholic fermentation yeast according to a first invention that achieves the above-described object is *Saccharomyces* having resistance to limonene.

The alcoholic fermentation yeast according to the first invention further has high-temperature resistance.

The alcoholic fermentation yeast according to the first invention may be *Saccharomyces Cerevisiae*.

The alcoholic fermentation yeast according to the first invention may be *Saccharomyces Cerevisiae* (Deposition No. NITE BP-890).

An ethanol production method according to a second invention that achieves the above-described object uses the alcoholic fermentation yeast according to the first invention.

In the ethanol production method according to the second invention, a citrus may be used as a starting material.

In the ethanol production method according to the second invention, a heavy liquid obtained by subjecting a citrus juice residue extract to three-phase centrifugation may be used as a starting material.

In the ethanol production method according to the second invention, a citrus juice residue extract containing an acidic material added thereto may be used as a starting material.

In the ethanol production method according to the second invention, the acidic material is preferably nitric acid.

Advantageous Effects of Invention

In the alcoholic fermentation yeast according to any of claims 1 to 4, its resistance to limonene is higher than that of a general yeast, so that ethanol can be produced efficiently.

In particular, in the alcoholic fermentation yeast according to claim 2, its resistance to high temperature is higher than that of the general yeast, so that ethanol can be produced efficiently at high temperature.

With the ethanol production method according to any of claims 5 to 9, ethanol can be produced from the starting material containing limonene more efficiently than when the general yeast is used.

In particular, with the ethanol production method according to claim 6 in which the citrus containing limonene is used as the starting material, ethanol can be produced more efficiently than when the general yeast is used.

In particular, with the ethanol production method according to claim 7, since the concentration of limonene is low, ethanol can be produced more efficiently.

In particular, with the ethanol production method according to claim 8, since the propagation of unwanted bacteria is suppressed, ethanol can be produced more efficiently.

In particular, with the ethanol production method according to claim 9, there is no fear of corrosion of steel materials used in an ethanol production apparatus.

BRIEF DESCRIPTION OF DRAWINGS

FIG. 1 is a diagram illustrating the base sequence of a BP-890 strain according to Example 1 of the present invention.

DESCRIPTION OF EMBODIMENTS

Figure 2:
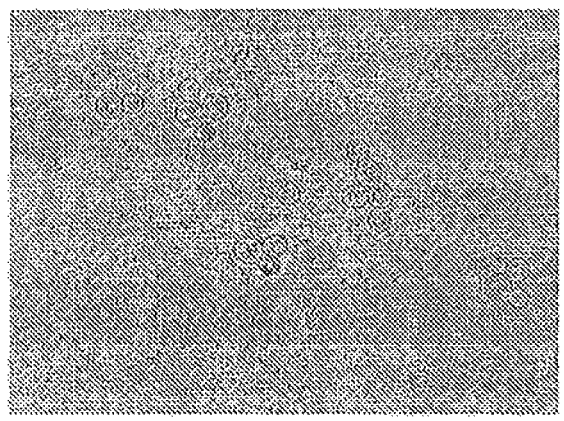
FIG. 2 is a microscope photograph of the BP-890 strain (1000× magnification).

Embodiments of the present invention will next be described with reference to the accompanying drawings, in order to provide an understanding of the present invention. An alcoholic fermentation yeast according to an embodiment of the present invention is *Saccharomyces* having limonene resistance. This alcoholic fermentation yeast further has high-temperature resistance. When ethanol is produced using the alcoholic fermentation yeast according to this embodiment, tangerine orange (an example of citrus fruits) is used as a starting material. However, the technical scope of the present invention is not construed to be limited by the following embodiments.

Hereinafter, the "limonene resistance" means a property of a yeast that allows ethanol fermentation at a yield of 86% or higher in the presence of limonene at a concentration of 0.1 to 0.5 wt % in a starting material. The "high-temperature resistance" means a property of a yeast that allows ethanol fermentation at a yield of 86% or higher in an environment with a fermentation temperature of 40° C. or higher. *Saccharomyces Cerevisiae* with no limonene resistance and no high-temperature resistance is referred also to as a "general yeast."

The present invention will next be described by way of Examples.

Example 1

Isolation of Novel Yeast

A tangerine orange juice residue extract was collected from a production line in a factory for juice of citrus fruits harvested in Ehime prefecture. This tangerine orange juice residue extract was diluted by a factor of 1,000, and the dilution was spread over a YPD agar culture medium (containing 1% of yeast extract, 2% of peptone, and 2% of glucose) and cultured at: 30° C. for about 2 days.

Various yeasts forming colonies on the culture petri dish were picked and subjected to pure culture on YPD culture mediums (containing 2% of yeast extract, 2% of peptone, and 10% of glucose, pH: 6.5 to 7.0).

(Screening of Yeasts)

A yeast having limonene resistance was screened from the pure cultured yeasts.

More specifically, ethanol fermentation was performed using several sugar solutions as starting materials with different limonene concentrations within the range of 0.02 to 0.2% v/v. Then strains having high ethanol fermentability in the sugar solutions with different limonene concentrations were selected as limonene resistant strains. Among these limonene resistant strains, a strain having particularly high limonene resistance was deposited (Deposition No. NITE BP-890). In the present description, the deposited strain is hereinafter referred to as a "BP-390 strain." The BP-890 strain has been deposited in the following depositary by the application filed by the present applicants.

(1) Name: NITE Patent Microorganisms Depositary (NPMD)

(2) Address; 2-5-8 Kazusakamatari, Kisarasu-shi, Chiba 292-0818 Japan (3) Phone number: 0438-20-5580

(4) Deposition No.: NITE BP-890

(5) Deposition No. at the time of original deposit: NITE P-890

(6) Date of original deposit: Jan. 28, 2010

(7) Conversion date under the Budapest Treaty: Jun. 3, 2011

(Identification of BP-890 Strain)

DNA was extracted from the BP-890 strain, and its D2LSUrDNA region was amplified by PCR. The base sequence of the obtained PCR product was determined by direct sequencing (see FIG. 1). On the basis of this base sequence, a BLAST search was performed on the D2LSUrDNA sequences of known microorganisms in a database to identify microorganisms estimated as closely-related species. As shown in the results in TABLE 1, the BP-890 strain was found to be a *Saccharomyces Cerevisiae* yeast.

YPD culture mediums, and the vertical axis represents the rate of ethanol production (%).

As is clear from the figure, with the general yeast, as the concentration of limonene increased, the ethanol production rate decreased. However, with the BP-890 strain, until the concentration of limonene added was about 0.1% v/v, the ethanol production rate was higher than 90%, and the ethanol production rate did not decrease.

TABLE 1

BLAST RESULT FOR BP-890 STRAIN

| Accession | Description | Max score | Total score | Query coverage | Max ident (HOMOLOGY) |
|---|---|---|---|---|---|
| AB362220.1 | *Saccharomyces cerevisiae* gene for 26S ribosomal RNA, partial sequence, strain: TY-2 | 578 | 578 | 99% | 99% |
| DQ888227.1 | Synthetic construct clone pNOY373 35S ribosomal RNA, 18S ribosomal RNA, 5.8S ribosomal RNA, 25S ribosomal RNA, and 5S ribosomal RNA, complete sequence | 578 | 578 | 99% | 99% |
| DQ674258.1 | *Saccharomyces cerevisiae* strain L68 28S ribosomal RNA gene, partial sequence | 578 | 578 | 99% | 99% |
| AY497669.1 | *Saccharomyces cerevisiae* strain CBS 1171 26S ribosomal RNA gene, partial sequence | 578 | 578 | 99% | 99% |
| J01355.1 | *Saccharomyces cerevisiae* 25S ribosomal RNA gene, complete sequence | 578 | 578 | 99% | 99% |
| AY046154.1 | *Saccharomyces cerevisiae* NRRL Y-12632 26S ribosomal RNA gene, partial sequence | 578 | 578 | 99% | 99% |
| AY529515.1 | *Saccharomyces cerevisiae* isolate 40 26S ribosomal RNA gene, partial sequence | 578 | 578 | 99% | 99% |
| Z73326.1 | *S.cerevisiae* chromosome XII reading frame ORF YLR154c | 578 | 578 | 99% | 99% |
| U53879.1 | *Saccharomyces cerevisiae* chromosome XII cosmid 9634 | 578 | 1156 | 99% | 99% |
| GQ121701.1 | *Saccharomyces cerevisiae* strain IMAU6Y152(DX11-2) 26S large subunit ribosomal RNA gene, partial sequence | 576 | 576 | 98% | 100% |
| GQ121699.1 | *Saccharomyces cerevisiae* strain IMAU6Y150(DX10-3) 26S large subunit ribosomal RNA gene, partial sequence | 576 | 576 | 98% | 100% |
| GQ121698.1 | *Saccharomyces cerevisiae* strain IMAU6Y149(DX10-2) 26S large subunit ribosomal RNA gene, partial sequence | 576 | 576 | 98% | 100% |
| GQ121692.1 | *Saccharomyces cerevisiae* strain IMAU6Y143(DX8-1) 26S large subunit ribosomal RNA gene, partial sequence | 576 | 576 | 98% | 100% |
| GQ121690.1 | *Saccharomyces cerevisiae* strain IMAU6Y141(DX7-3) 26S large subunit ribosomal RNA gene, partial sequence | 576 | 576 | 98% | 100% |
| GQ121688.1 | *Saccharomyces cerevisiae* strain IMAU6Y139(DX7-1) 26S large subunit ribosomal RNA gene, partial sequence | 576 | 576 | 98% | 100% |

(Mycological Properties)

The BP-890 strain has the following mycological properties.
1. Cell shape: Spherical (see FIG. 2)
2. Colony shape: White (no gloss), wrinkled.
3. Proliferation form: multilateral budding
4. Optimal growth temperature; 30° C.
5. Optimal growth pH: 4.0
6. Cohesiveness: No
7. Fermentable sugars: sucrose, glucose, and fructose Example 2

Limonene Resistance Test

Figure 3:
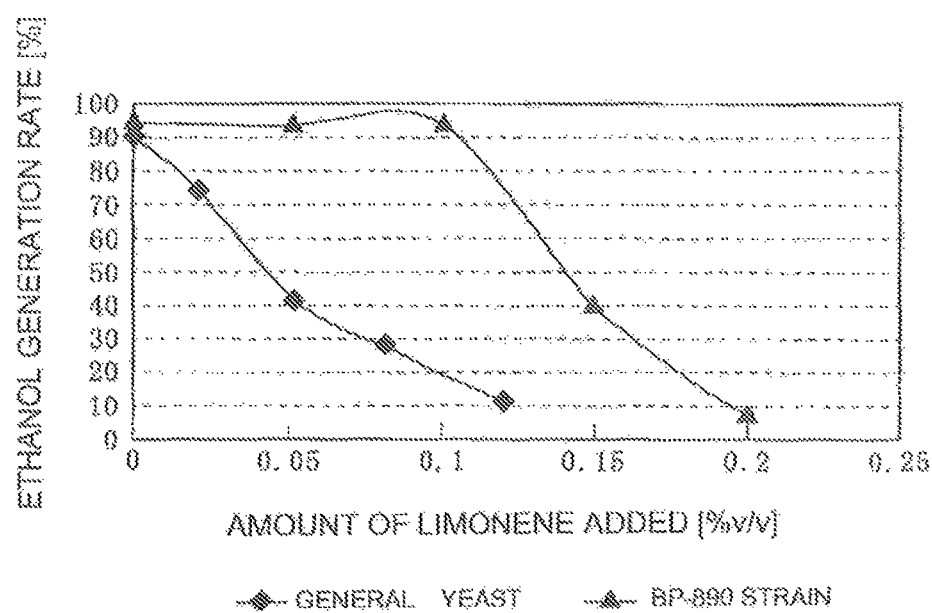
FIG. 3 is a graph showing the limonene resistance of the BP-890 strain.

The BP-890 strain was subjected to batch fermentation (shake culture) with limonene added at different concentrations to examine ethanol fermentability. The experimental conditions are as follows.
<Experimental Conditions>
1. Fermentation temperature: 30° C.
2. Shake rate: 120 rpm (amplitude: 10 mm)
3. Fermentation time: 24 hours
4. Starting material: YPD culture medium The results are shown in FIG. 3. In FIG. 3, the horizontal axis represents the amount (% v/v) of limonene added to the (High-Temperature Resistance Test)

Figure 4:
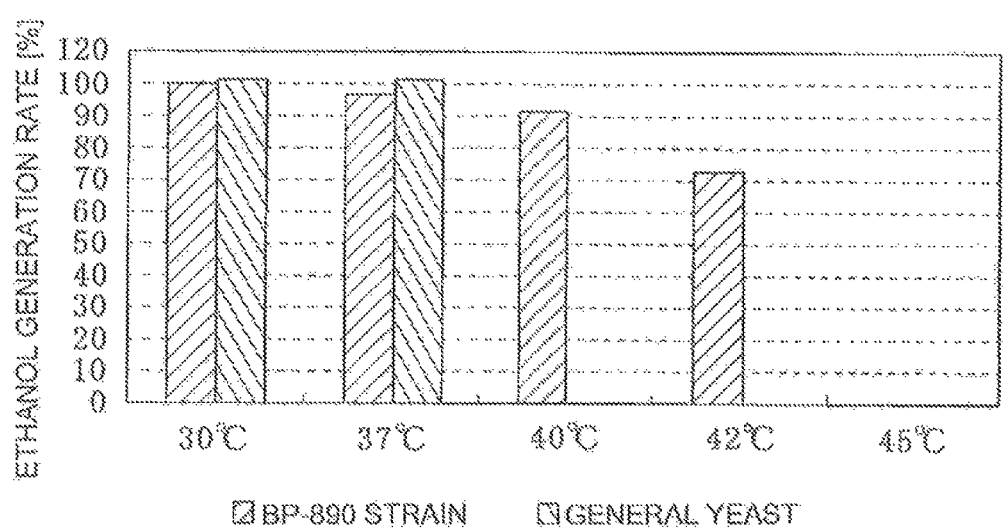
FIG. 4 is a graph showing the high-temperature resistance of the BP-890 strain.

24 Hour batch fermentation experiments were performed using YPD culture mediums at fermentation temperatures of 30° C., 37° C., 40° C., 42° C., and 45° C. The experimental conditions are as follows.
<Experimental Conditions>
1. Shake rate; 120 rpm (amplitude: 10 mm)
2. Fermentation time: 24 hours
3. Starting material: YPD culture medium The results are shown in FIG. 4. In the figure, the horizontal axis represents temperature, and the vertical axis represents the rate of ethanol production. There are portions in which the ethanol production rate is slightly higher than 100%. These large ethanol production rates may be due to measurement error.

As is clear from the figure, the general yeast was capable of fermentation only up to a fermentation temperature of 37° C. However, the BP-890 strain was capable of fermentation up to a fermentation temperature of 40° C. at a high yield of 90% or higher. More specifically, the BP-890 strain was found to have high-temperature resistance. In addition, the ethanol production rate of the BP-890 strain was about 70% even at 42° C., and the BP-890 was found to be capable of fermentation even at 42° C. at a relatively high yield.

(Ethanol Fermentation Test [1])

Batch culture was performed in the presence of limonene to examine ethanol production and growth of the yeasts. The experimental conditions are as follows.

<Experimental Conditions>
1. Fermentation temperature: 30° C.
2. Stirring rate: 120 rpm
3. Fermentation time: 24 hours
4. Starting material: Heavy liquid obtained by three-phase centrifugation of tangerine orange (Citrus unshiu) juice residue extract (pH is adjusted to 3.5)

Figure 5A:
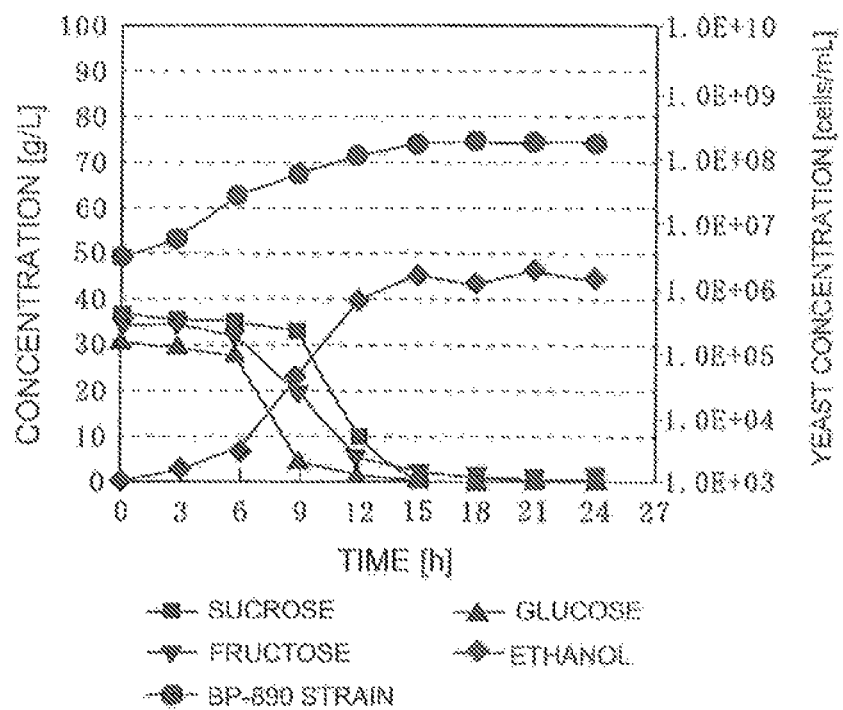
FIGS. 5(A) and 5(B) are a graph showing the batch fermentation characteristics of the BP-890 strain and a graph showing the batch fermentation characteristics of a general yeast, respectively.

The results for the BP-890 strain are shown in FIG. 5(A). In FIG. 5, the horizontal axis represents time, and the vertical axis represents the concentrations (g/L) of sucrose, glucose, fructose, and ethanol and the concentration (cells/ml) of the yeast.

Figure 5B:
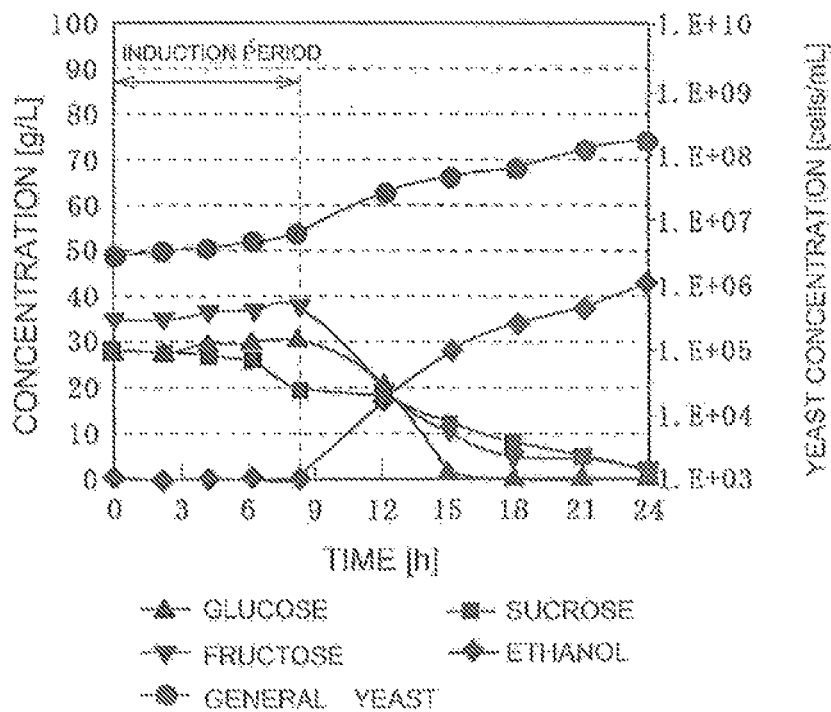

As shown in FIG. 5(B), the general yeast exhibited an induction period of about 8 hours. However, the BP-890 strain exhibited no induction period, and the proliferation started immediately after the start of culture. The yeast proliferation rate and the ethanol production rate were higher with the BP-890 strain than with the general yeast. Because of these characteristics, the use of the BP-890 strain for ethanol fermentation allows culture to be performed more stably and in a shorter period of time than when the general yeast is used and also allows efficient fermentation with a short residence time to be performed.

Ethanol production was similarly examined using the following three starting materials prepared from this tangerine juice residue extract under different conditions, i.e., with or without three-phase centrifugation and with or without addition of nitric acid.

(1) Tangerine orange juice residue extract having a pH of 3.5 adjusted by addition of nitric acid (no three-phase centrifugation)
(2) Heavy liquid obtained by three-phase centrifugation of tangerine orange juice residue extract (no pH adjustment)
(3) Tangerine orange juice residue extract (no three-phase centrifugation and no pH adjustment)

The effect of the three-phase centrifugation is removal of limonene. The BP-890 strain has limonene resistance. Therefore, it seems that the removal of limonene is unnecessary. However, the condition that whether or not a tangerine orange juice residue extract has been subjected to three-phase centrifugation is considered because of the following reasons: (1) although the BP-890 strain has limonene resistance, the ethanol production rate is expected to be further improved when the limonene concentration is low, and (2) limonene cannot be removed completely by three-phase centrifugation. The effect of the addition of nitric acid is suppression of propagation of unwanted bacteria. The details of the effects of three-phase centrifugation and the addition of nitric acid will be described later.

The results under these conditions are shown in TABLES 2 to 4.

TABLE 2

ETHANOL FERMENTATION TEST RESULTS (CENTRIFUGATION: NO, pH ADJUSTMENT: YES)

| | | SUCROSE [g/L] | GLUCOSE [g/L] | FRUCTOSE [g/L] | TOTAL OF THREE SUGARS [g/L] | ETHANOL [g/L] | ETHANOL PRODUCTION RATE [%] |
|---|---|---|---|---|---|---|---|
| GENERAL YEAST | BEFORE FERMENTATION | 22.9 | 30.4 | 30.0 | 83.3 | 0.0 | — |
| | AFTER FERMENTATION | 0.0 | 0.0 | 1.2 | 1.2 | 39.2 | 92.1 |
| BP-890 STRAIN | BEFORE FERMENTATION | 27.0 | 20.5 | 26.3 | 73.8 | 4.9 | — |
| | AFTER FERMENTATION | 1.9 | 0.0 | 2.3 | 4.1 | 43.9 | 103.5 |

TABLE 2 shows the results of the measurement of the concentrations (g/L) of sucrose, glucose, fructose, and ethanol before and after fermentation and the ethanol production rate (%) for each of the general yeast and the BP-890 strain.

TABLE 3

ETHANOL FERMENTATION TEST RESULTS (CENTRIFUGATION: YES, pH ADJUSTMENT: NO)

| | | SUCROSE [g/L] | GLUCOSE [g/L] | FRUCTOSE [g/L] | TOTAL OF THREE SUGARS [g/L] | ETHANOL [g/L] | ETHANOL PRODUCTION RATE [%] | AVERAGE ETHANOL PRODUCTION RATE [%] |
|---|---|---|---|---|---|---|---|---|
| GENERAL YEAST | BEFORE FERMENTATION | 23.2 | 15.1 | 14.1 | 52.5 | 0.0 | — | — |
| | AFTER FERMENTATION | 0.0 | 5.3 | 1.8 | 7.0 | 24.3 | 90.7 | 89.9 |
| | AFTER FERMENTATION | 0.0 | 6.3 | 1.3 | 7.7 | 23.9 | 89.0 | |
| BP-890 STRAIN | BEFORE FERMENTATION | 22.5 | 14.6 | 13.6 | 50.7 | 0.0 | — | — |
| | AFTER FERMENTATION | 0.0 | 0.0 | 2.0 | 2.0 | 23.6 | 90.9 | 94.1 |
| | AFTER FERMENTATION | 0.0 | 0.0 | 2.1 | 2.1 | 25.2 | 97.3 | |

TABLE 3 shows the results of the measurement of the concentrations (g/L) of sucrose, glucose, fructose, and ethanol before and after fermentation and the ethanol production rate (%) for each of the general yeast and the BP-890 strain.

Data were measured twice after fermentation and represented as "after fermentation (1)" and "after fermentation (2)." An average ethanol production rate (%) is the average of the two measured ethanol production rates (%).

TABLE 4

ETHANOL FERMENTATION TEST RESULTS (CENTRIFUGATION: NO, pH ADJUSTMENT: NO)

|  |  | SUCROSE [g/L] | GLUCOSE [g/L] | FRUCTOSE [g/L] | TOTAL OF THREE SUGARS [g/L] | ETHANOL [g/L] | ETHANOL PRODUC- TION RATE [%] | AVERAGE ETHANOL PRODUC- TION RATE [%] |
|---|---|---|---|---|---|---|---|---|
| GENERAL YEAST | BEFORE FERMENTATION | 25.1 | 23.9 | 28.3 | 77.3 | 0.0 | — | — |
|  | AFTER FERMENTATION | 0.0 | 11.2 | 2.2 | 13.4 | 15.0 | 38.1 | 36.0 |
|  | AFTER FERMENTATION | 0.0 | 12.5 | 6.5 | 19.0 | 13.4 | 34.0 |  |
| BP-890 STRAIN | BEFORE FERMENTATION | 25.1 | 23.9 | 28.3 | 77.3 | 0.0 | — | — |
|  | AFTER FERMENTATION | 0.0 | 9.1 | 1.7 | 10.8 | 21.5 | 54.4 | 50.9 |
|  | AFTER FERMENTATION | 0.0 | 10.8 | 3.1 | 13.9 | 18.7 | 47.3 |  |

TABLE 4 shows data similar to the data in TABLE 3.

As is clear from the results in TABLES 2 to 4, the ethanol production rates were higher with the BP-890 strain than with the general yeast. In particular, for the tangerine orange juice residue extract with no centrifugation treatment and no pH adjustment (untreated starting material), when the BP-890 strain was used, the ethanol production rate was higher by 15% than that with the general yeast (see TABLE 4). In TABLE 2, ethanol was present before fermentation. This is because ethanol contained in a cultured yeast solution added to the starting material was detected.

(Ethanol Fermentation Test [2])

Fed batch culture was performed using a heavy liquid obtained by three-phase centrifugation of a tangerine orange juice residue extract as a starting material to examine ethanol production and the grown of yeast. The experimental conditions are as follows.

Figure 6:
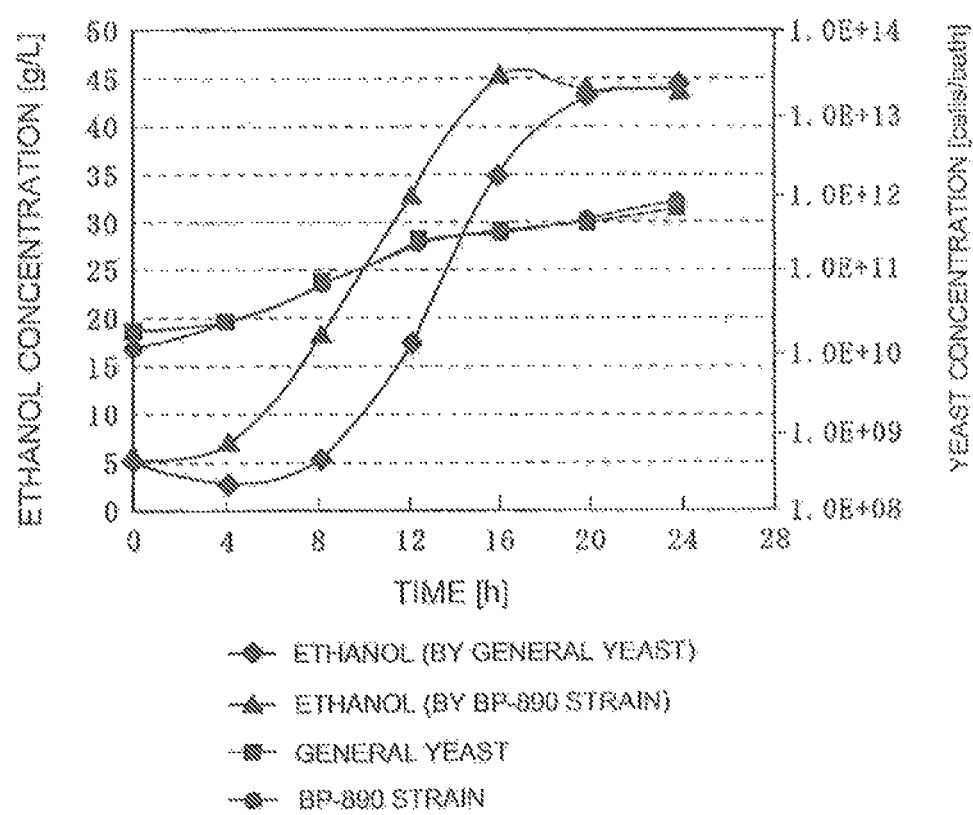
FIG. 6 is a graph showing the ethanol fermentation characteristics of the BP-890 strain in fed batch culture.

<Experimental Conditions>
 1. Temperature: 30° C.
 2. Stirring rate: 150 rpm
 3. Starting material supply: 3.3 ml/min
 4. Reactor volume: 5 L
 5. Amount of air blown: 0.05 vvm
 6. Amount of yeast, added: 3.0% v/v
 7. Starting material: tangerine orange (Citrus unshiu) juice residue extract The results are shown in FIG. 6. In FIG. 6, the horizontal axis represents time, and the vertical axis represents the ethanol concentration (g/L) and the yeast concentration (cells/bath).

As is clear from the figure, the solution subjected to three-phase centrifugation and having a low limonene concentration exhibited an induction period of about 4 hours when the general yeast was used. However, when the BP-890 strain was used, there was no induction period, and proliferation started immediately after the start of culture.

With the BP-890 strain, ethanol production was started immediately after the start of culture and reached a peak at 15 hours. More specifically, with the BP-890 strain, the ethanol production rate was found to be higher than that with the general yeast. In other words, the BP-890 strain exhibits no induction period even when used for a starting material subjected to three-phase centrifugation and having a low limonene concentration and allows stable fermentation.

Example 3

Ethanol Production [1] Using BP-890 Strain

Ethanol was produced using the BP-890 strain and iyokan as an example of the starting material. A description will first be given of a production method.

Figure 7:
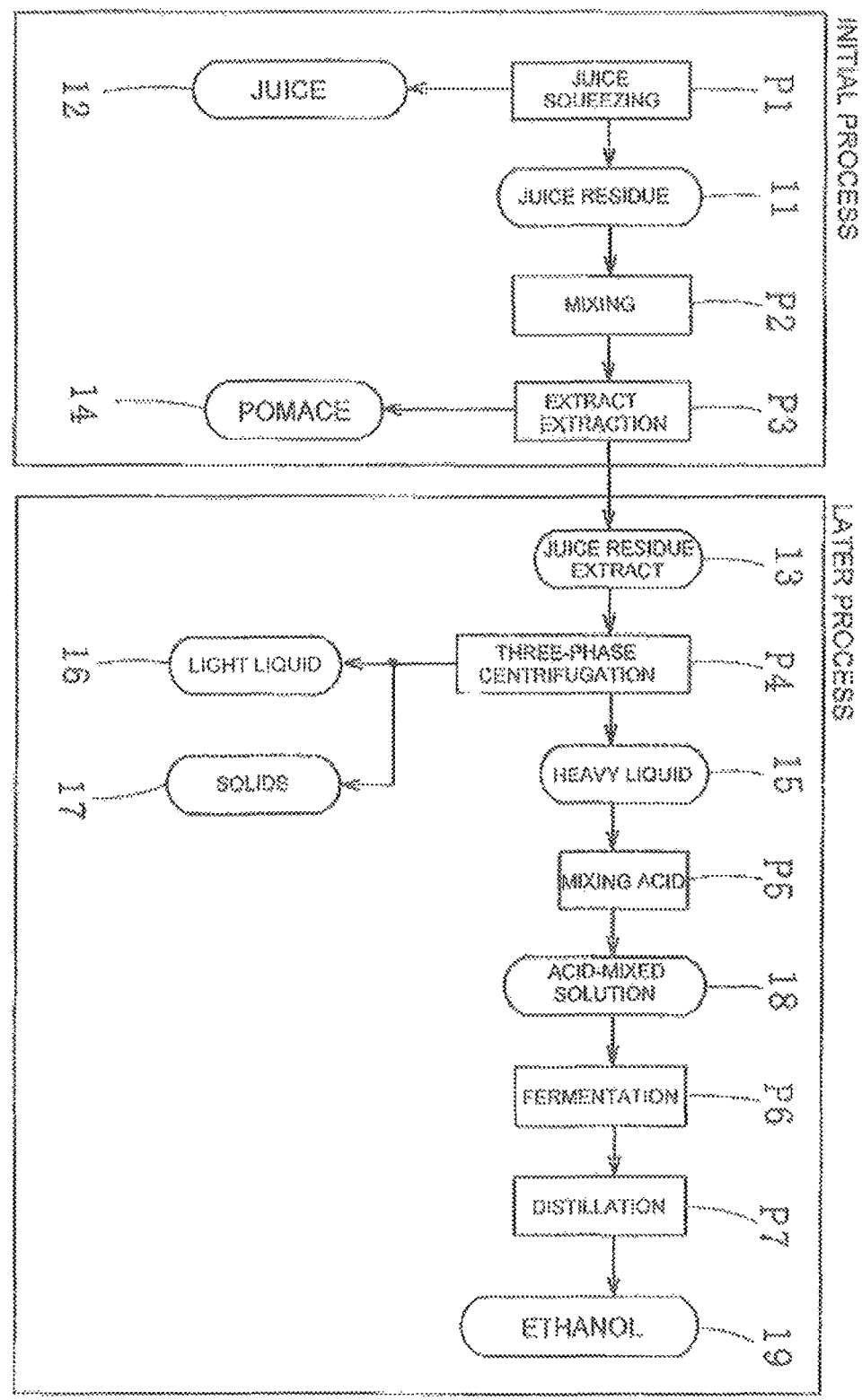
FIG. 7 is a process chart showing steps in an ethanol production method in Example 3 of the present invention.

The ethanol production method includes an initial process and a later process as shown in FIG. 7. The initial process includes a juice squeezing step P1, a mixing step P2, and an extract extracting step P3. The later process includes a three-phase centrifugation step P4, an acid mixing step P5, a fermentation step P6, and a distillation step P7. Each of these steps will next be described.

The juice squeezing step P1 is a step of squeezing the iyokan using a juice squeezing machine such as an in-line type or chopper pulper type machine. In this step, juice residue 11 and juice 12 are produced.

The mixing step P2 is a step of mixing the juice residue 11 produced in the juice squeezing step P1 with slaked lime being an example of an alkaline material. Since the juice residue 11 produced in the juice squeezing step P1 is in a gel or slurry form, an extract cannot be extracted efficiently using a press. However, the addition and mixing of the slaked lime allows the extract to be extracted efficiently.

The extract extracting step P3 is a step of pressing the juice residue 11 that has been treated so as to be easily pressed in the mixing step P2 to thereby subject the juice residue 11 to dewatering treatment. In this step, a juice residue extract 13 and pomace 14 are produced.

The three-phase centrifugation step P4 is a step of subjecting the juice residue extract 13 produced in the extract extracting step P3 to three-phase centrifugation to form a heavy liquid 15, a light liquid 16, and solids 17.

In the three-phase centrifugation step P4, limonene, or a fermentation inhibitor, contained in the juice residue extract 13 is removed together with the light liquid (oily substance) 16 and the solids 17. In this manner, the limonene concentration in the liquid part of the heavy liquid 15 can be reduced to 0.01 wt % or lower, and the overall concentration of limonene including limonene in solids in the heavy liquid 15 can be reduced to 0.1 wt % or lower.

By subjecting the juice residue extract 13 to three-phase centrifugation to remove the fermentation inhibitor in this step, the proliferation properties of the yeast during ethanol fermentation is improved. The fermentability is thereby stabilized, and the ethanol production rate is increased.

Since the three-phase centrifuge used in this step separates the light liquid and heavy liquid with a small difference in specific gravity, it is preferable that the three-phase centrifuge used in this step be a disk-type centrifuge that can have a large sedimentation area. When a centrifugal force of 5,000 G or larger is available, the separation can be industrially performed.

The acid mixing step P5 is a step of mixing the heavy liquid 15 produced in the three-phase centrifugation step P4 with nitric acid which is an example of an acidic material to form an acid-mixed solution 18. More specifically, in this step, 60% concentrated nitric acid is added to the heavy liquid 15 produced in the three-phase centrifugation step P4, and the mixture is stirred and mixed using a stirring pump or a stirrer. The pH of the heavy liquid 15 is thereby adjusted to 3.5, and the acid-mixed solution 18 is produced.

Since the specific gravity of nitric acid is larger than the specific gravity of the heavy liquid 15 produced in the three-phase centrifugation step P4, the mixture is continuously or regularly stirred after the addition of nitric acid.

In this step, the amount of unwanted bacteria in the acid-mixed solution 18 is reduced to about 1/10 to 1/1,000 of the amount before the addition of nitric acid. The pH after adjustment is set in consideration of the facts that (1) the optimal pH for the life of unwanted bacteria is 5.0 to 7.0 and (2) the optimal pH for the growth of the yeast necessary for ethanol fermentation in the next step is 3.5 to 6.0. More specifically, in this step, the pH is adjusted such that the yeast can grow with the propagation of unwanted bacteria suppressed. Such a pH is, for example, 3.0 to 4.0.

The fermentation step P6 is a step of adding the *Saccharomyces Cerevisiae* BP-890 strain to the heavy liquid 15 (the acid-mixed solution 18) with its pH adjusted in the acid mixing step P5 to thereby perform ethanol fermentation. The fermentation in this step is continuous fermentation but may be batch fermentation.

The distillation step P7 is a step of distilling the ethanol fermentation solution produced in the fermentation step P6. In this step, ethanol 19 can be purified.

Ethanol was produced using the BP-890 strain according to the above-described production steps.

First, in the juice squeezing step P1, iyokan used as the starting material was squeezed. Next, in the mixing step P2, slaked lime was mixed into the produced juice residue 11. Then, in the extract extracting step P3, the juice residue 11 containing slaked lime mixed thereinto was pressed to produce a juice residue extract 13. Next, in the three-phase centrifugation step P4, the juice residue extract 13 produced in the extract extracting step P3 was subjected to a three-phase centrifuge to separate a heavy liquid 15. Then, in the acid mixing step P5, nitric acid was added to the heavy liquid 15 to adjust its pH to 3.5, and the mixture was stirred for 2 hours to produce an acid-mixed solution 18. Then, in the fermentation step P6, continuous fermentation was performed.

Figure 8:
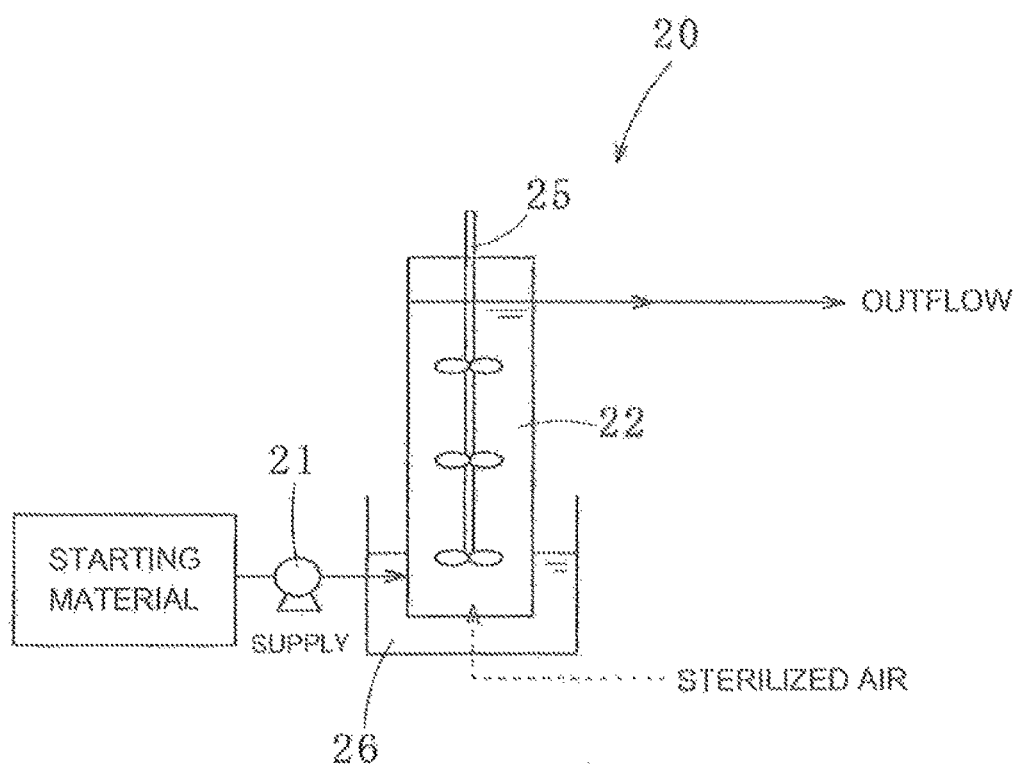
FIG. 8 is a diagram illustrating the schematic configuration of a continuous fermentation apparatus used in an ethanol fermentation step.

A continuous fermentation apparatus 20 used in the fermentation step P6 will next be described. As shown in FIG. 8, in the fermentation step P6, the acid-mixed solution 18 (pH: 3.5) used as the starting material was fed from a pump 21 to a bioreactor 22. In the bioreactor 22, continuous fermentation (average residence time: 24 hours) was performed. The fermented solution overflowed from the upper part of the continuous fermentation apparatus 20. During fermentation, sterilized air was blown into the fermented solution in the bioreactor 22. The fermented solution was continuously stirred using a three-blade impellor 25. The temperature inside the bioreactor 22 was maintained by a thermostatic bath 26.

Figure 9:
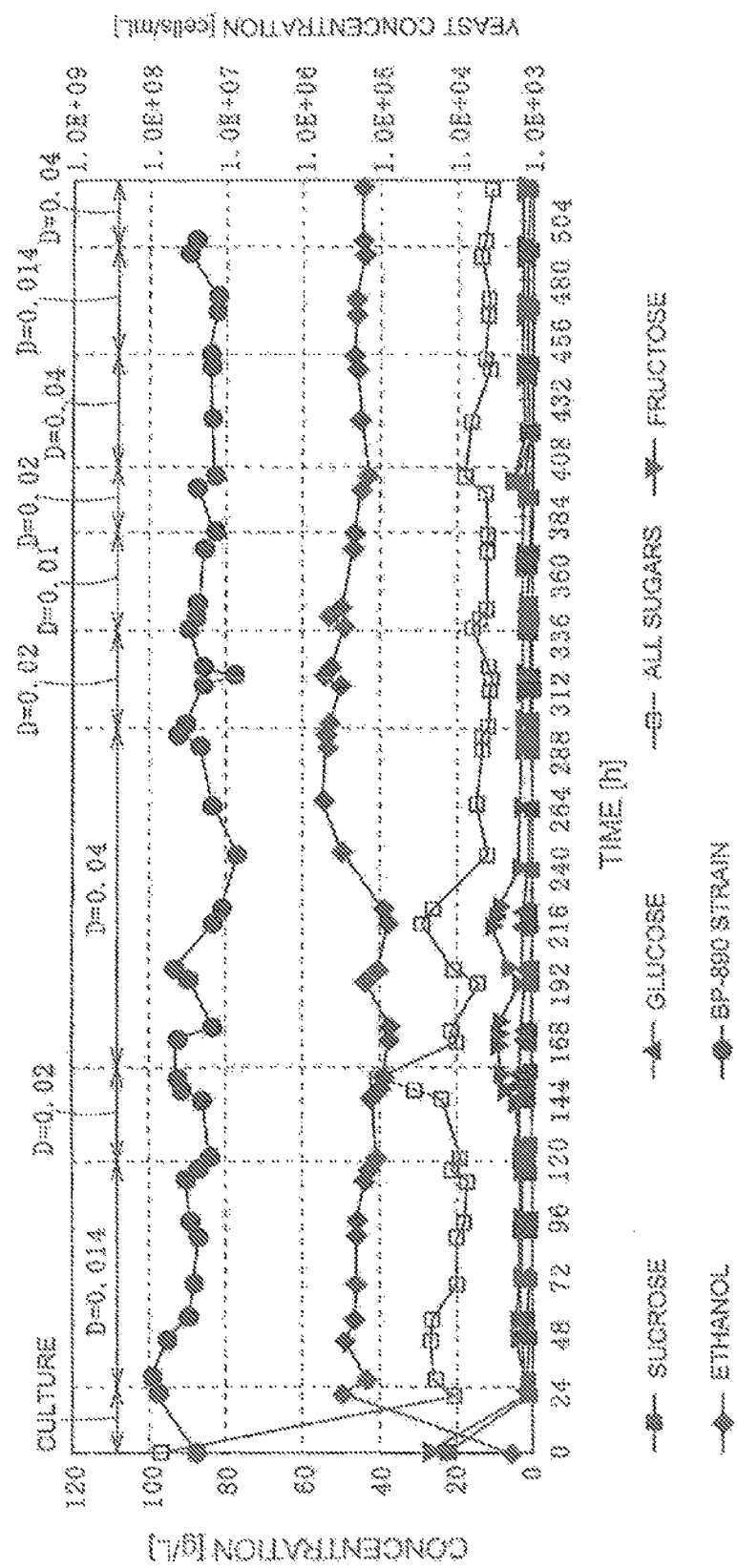
FIG. 9 is a graph (1) showing the results of ethanol production.

The detailed fermentation conditions are as follows.
<Continuous Fermentation Conditions>
 1. Fermentation temperature: 30° C.
 2. Stirring rate: 150 rpm
 3. Fermentation time: 24 hours (residence time)
 4. Amount of yeast added: 3.0% v/v
 5. Reactor volume: 5 L
 6. Dilution ratio: 0.04 (l/h)
 7. Amount of sterilized air blown: 0.05 vvm
 8. Other: the dilution ratio was changed in the range of 0.014 to 0.04 during continuous fermentation The results are shown in FIG. 9. In FIG. 9, the horizontal axis represents time elapsed, and the vertical axis represents the concentrations (g/L) of sucrose, glucose, fructose, and ethanol, the total concentration (g/L) of all the sugars, and the concentration (cells/ml) of the yeast.

In this Example, the dilution ratio D was changed in the range of 0.014 to 0.04. However, ethanol was produced stably irrespective of the changes in the dilution ratio D. Generally, when the dilution ratio D is changed during continuous fermentation using the general yeast, fermentability becomes unstable, and the amount of ethanol produced and the amount of the yeast decrease as the time elapses, so that fermentation failure occurs. The average ethanol production rate was 105.4%. The average ethanol production rate exceeded 100%. This may be because of the following two reasons. First, the sugars taken into account to compute the average ethanol production rate were sucrose, glucose, and fructose, but the yeast fermented sugars other than these sugars. Second, the average ethanol production rate was computed to be larger due to measurement error.

Example 4

Ethanol Production [2] Using BP-890 Strain

This Example is different from Example 3 in the following two points. The centrifugation step P4 was omitted, and the range of the changes in the dilution ratio D was changed. More specifically, after a juice residue extract was produced in the extract extracting step P3, the centrifugation step P4 was omitted, and nitric acid was added to the juice residue extract in the acid mixing step P5 to produce an acid-mixed solution having a pH of 3.5. The acid-mixed solution was fed to the bioreactor 22 to perform the fermentation step P6. The concentration of limonene in the acid-mixed solution prepared by adjusting the pH of the juice residue extract 13 (the total of the concentration of limonene adhering to the solids and the concentration of limonene present in the solution) was 0.2% v/v.

Figure 10:
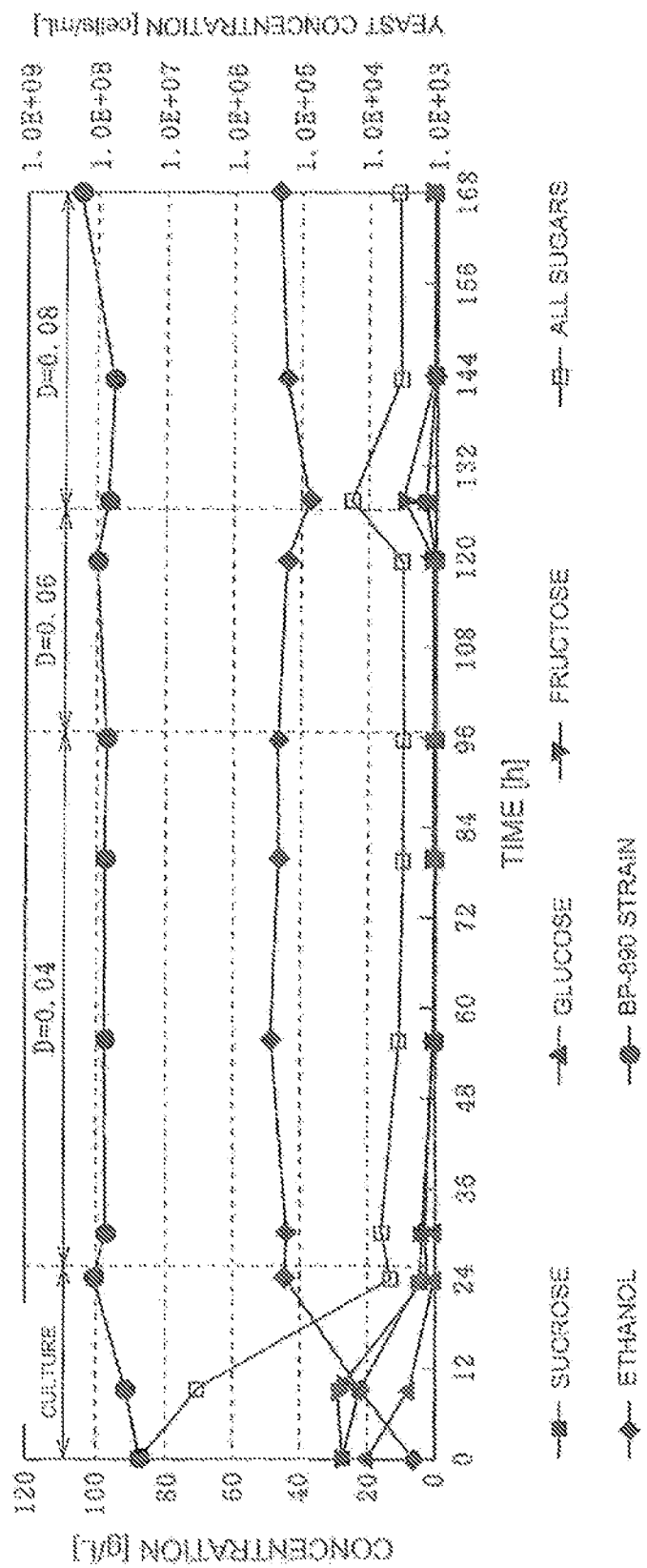
FIG. 10 is a graph (2) showing the results of ethanol production.

The results are shown in FIG. 10. In FIG. 10, the horizontal axis represents time elapsed (h), and the vertical axis represents the concentrations (g/L) of sucrose, glucose, fructose, and ethanol, the total concentration (g/L) of all the sugars, and the concentration (cells/ml) of the yeast.

In this example, the dilution ratio D was changed in the range of 0.04 to 0.08. However, ethanol was produced stably irrespective of the changes in the dilution ratio D. The average ethanol production rate was 88.5%.

Example 5

Ethanol Production [3] Using BP-890 Strain

In this example, the operating conditions of the continuous fermentation apparatus 20 (see FIG. 8) are different from those in Example 3 above. More specifically, the general yeast and the BP-890 strain were used, and continuous fermentation was performed for each of these yeasts under the operating conditions in which the fermentation treatment was suspended and resumed repeatedly according to the operation of the juice factory. The concentration of limonene in the acid-mixed solution prepared by adjusting the pH of the juice residue extract 13 was about 0.03 vol %.

The details of the operating conditions of the continuous fermentation apparatus 20 are as follows.

<Operating Conditions>

1. A fermentation period (12 hours) in which ethanol fermentation is performed and a suspended period (12 hours) in which the supply of the starting material is stopped to suspend the fermentation are repeated (the processing of the starting material is performed for a half day, and the processing is suspended for another half day).

2. The dilution ratio D during the fermentation period is 0.03 (average residence time: 12 hours).

3. During the suspended period, the temperature inside the bioreactor 22 is maintained at 30° C. The stirring and the blowing of sterilized air are continued (only the supply of the starting material is suspended).

Figure 11A:
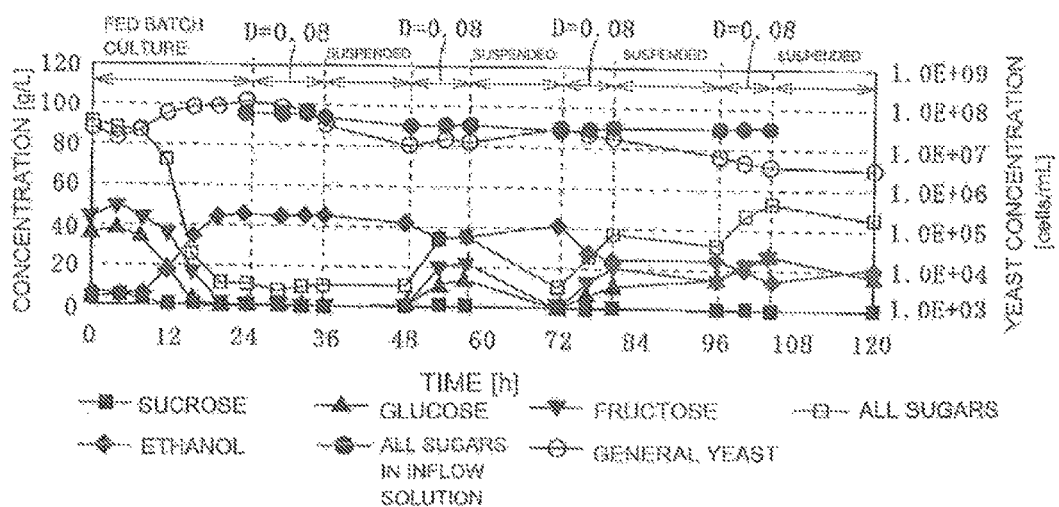
FIGS. 11(A) and 11(B) are a graph (3) showing the results of ethanol production by the general yeast and a graph (4) showing the results of ethanol production by the BP-890 strain, respectively.
Figure 11B:
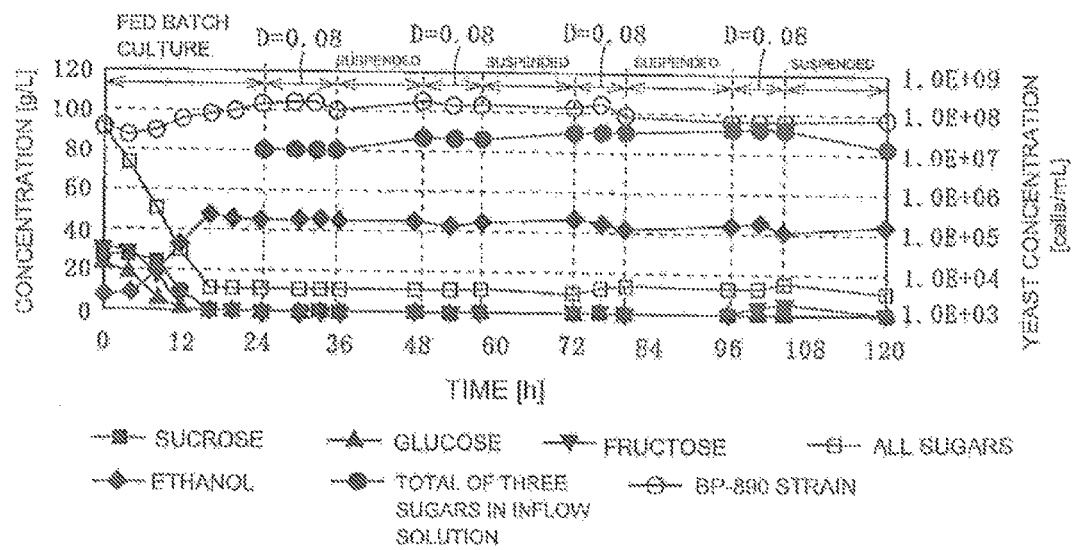

The results using the general yeast and the BP-890 strain are shown in FIGS. 11(A) and 11(B). In FIG. 11(A), the horizontal axis represents time elapsed (h), and the vertical axis represents the concentrations (g/L) of sucrose, glucose, fructose, and ethanol, the total concentration (g/L) of all the sugars, the total concentration (g/L) of all the sugars in an inflow solution, and the concentration (cells/ml) of the yeast.

In FIG. 11(B), the horizontal axis represents time elapsed (h), and the vertical axis represents the concentrations (g/L) of sucrose, glucose, fructose, and ethanol, the total concentration (g/L) of all the sugars, the total concentration (g/L) of these three sugars in an inflow solution, and the concentration (cells/ml) of the yeast.

In this Example, when the supply of the starting material was suspended in the presence of limonene which is the growth inhibitor, the growth of the general yeast with no limonene resistance was inhibited by limonene and also adversely affected by malnutrition etc. This caused a significant reduction in the growth rate of the yeast and the death of the yeast, and the amount of the yeast thereby decreased. Then the fermentability deteriorated. However, with the BP-890 strain, no reduction in the amount of the yeast was found even when the supply of the starting material was suspended, and high fermentability was maintained stably. More specifically, stable operation is impossible with the general yeast under the conditions in which the supply of the starting material is suspended temporarily, for example, suspended at night according to the operation of a juice factory. However, the BP-890 strain having limonene resistance was found to allow stable fermentation even under such conditions.

The present invention is not limited to the above-described embodiments and Examples, and any modification can be made so long as the gist of the invention is not changed.

In Examples 3 and 4 described above, ethanol fermentation was performed using the juice residue extract 13 obtained in the extract extracting step P3. However, ethanol fermentation (solid fermentation) may be performed using, as the starting material, the juice residue 11 obtained in the juice squeezing step P1.

REFERENCE SIGNS LIST

11: juice residue, 12: juice, 13: juice residue extract, 14: pomace, 15: heavy liquid, 16: light liquid, 17: solids, 18: acid-mixed solution, 19: ethanol, 20: continuous fermentation apparatus, 21: pump, 22: bioreactor, 25: three-blade impeller, 26: thermostatic bath

---

---

The invention claimed is:

1. A method of producing ethanol comprising:
   squeezing a citrus to produce a juice residue;
   mixing the juice residue with slaked lime;
   dewatering the juice residue mixed with the slaked lime by pressing the juice residue to produce a juice residue extract; and (1) mixing the juice residue extract with nitric acid to form an acid-mixed solution having a pH of 3.0 to 4.0 without subjecting the juice residue extract to a three-phase centrifugation, and then adding *Saccharomyces Cerevisiae* as an alcoholic fermentation yeast having a limonene resistance to the acid-mixed solution to perform alcoholic fermentation and to produce the ethanol, or (2) subjecting the juice residue extract to a three-phase centrifugation to form a heavy liquid, a light liquid and a solid, then mixing the heavy liquid with nitric acid to form an acid-mixed solution having a pH of 3.0 to 4.0, and adding *Saccharomyces Cerevisiae* as an alcoholic fermentation yeast having a limonene resistance to the acid-mixed solution to perform alcoholic fermentation and to produce the ethanol.

2. The method according to claim 1, wherein the alcoholic fermentation is a continuous fermentation performed at a dilution ratio of from 0.04 to 0.08 per hour.

3. The method according to claim 2, wherein the alcoholic fermentation yeast is *Saccharomyces Cerevisiae* (Deposition No. NITE BP-890).

4. The method according to claim 1, wherein the heavy liquid in the three-phase centrifugation comprises limonene having a concentration of 0.01 wt % or lower.

5. The method according to claim 4, wherein the centrifuge is a disk-type centrifuge.

6. The method according to claim 5, wherein a centrifugal force of the disk-type centrifuge is 5000 G or larger.

* * * * *

SEQUENCE LISTING

<160> NUMBER OF SEQ ID NOS: 1

<210> SEQ ID NO 1
<211> LENGTH: 325
<212> TYPE: DNA
<213> ORGANISM: Saccharomyces cerevisiae

<400> SEQUENCE: 1

```
tctttgtccg tgtttcaaga cgggcggcat ataaccatta tgccagcatc cttgacttac      60
gtcgcagtcc tcagtcccag ctggcagtat tcccacaggc tataatactt accgaggcaa     120
gctacattcc tatggattta tcctgccacc aaaactgatg ctggcccagt gaaatgcgag     180 attccctac ccacaaggag cagagggcac aaaacaccat gtctgatcaa atgcccttcc      240
ctttcaacaa tttcacgtac tttttcactc tctttcaaa gttctttca tctttccatc       300 actgtacttg ttcgctatcg gtcta                                          325
```